United States Patent [19]
Maeda et al.

[11] Patent Number: 5,698,699
[45] Date of Patent: Dec. 16, 1997

[54] PROCESSES FOR PRODUCTION OF QUINOLINE OR QUINAZOLINE DERIVATIVES AND INTERMEDIATES THEREFOR

[75] Inventors: Yoshiharu Maeda; Atsushi Inagaki, both of Osaka, Japan

[73] Assignee: Takeda Chemical Industries, Ltd., Osaka, Japan

[21] Appl. No.: 525,617

[22] PCT Filed: Jun. 19, 1995

[86] PCT No.: PCT/JP95/01210

§ 371 Date: Sep. 26, 1995

§ 102(e) Date: Sep. 26, 1995

[87] PCT Pub. No.: WO96/00223

PCT Pub. Date: Jan. 4, 1996

[30] Foreign Application Priority Data

Jun. 24, 1994 [JP] Japan ................................. 6-143433

[51] Int. Cl.$^6$ ................... C07D 215/20; C07D 215/12; C07D 239/72; C07D 239/76
[52] U.S. Cl. ................... 546/153; 546/156; 546/167; 544/283; 514/259; 514/314
[58] Field of Search ................... 546/153, 156, 546/167; 544/283; 514/259, 314

[56] References Cited

U.S. PATENT DOCUMENTS 5,436,247  7/1995  Sohda ........................ 514/259

FOREIGN PATENT DOCUMENTS 0 608 870   8/1994   European Pat. Off. .
49-117470  11/1974   Japan .
WO 94/02476  2/1994   WIPO .

OTHER PUBLICATIONS

Astlefore et al., "Synthesis of 1–Alkyl–1,2,4–triazoles: A New One–Pot Regiospecific Procedure", J. Org. Chem., vol. 54, No. 3, 1989, pp. 731–732.

Primary Examiner—C. Warren Ivy
Assistant Examiner—D. Margaret M. Mach
Attorney, Agent, or Firm—Foley & Lardner

[57] ABSTRACT

Processes for production of quinoline or quinazoline derivatives and intermediates therefor

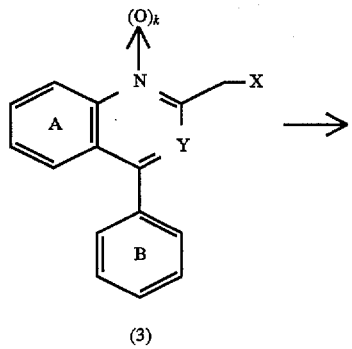

(3)

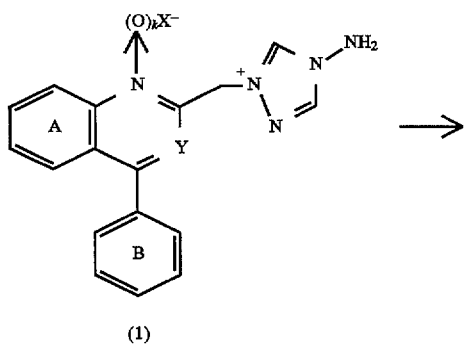

(1)

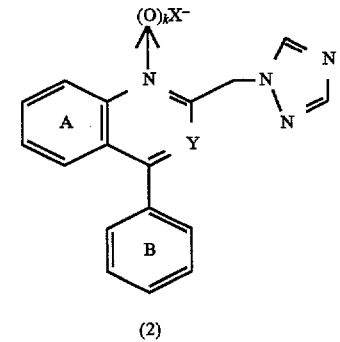

(2)

A process for producing a compound of formula (2) of value as antiinflammatory agents, which comprises reacting a compound of formula (3) or a salt thereof with 4-amino-1, 2,4-triazole to give a compound of formula (1) or a salt thereof and deaminating the same, and an intermediate compound (1).

In the above formulas, Y represents N or C-G in which G represents carboxyl which may be esterified or amidated, acyl, hydroxyalkyl which may be protected, or halogen; ring A and ring B each may be substituted; k is equal to 0 or 1; X represents a leaving group.

14 Claims, No Drawings

PROCESSES FOR PRODUCTION OF QUINOLINE OR QUINAZOLINE DERIVATIVES AND INTERMEDIATES THEREFOR

This application is a 371 of PCT/JP95/01210, filed 19 Jun. 1995.

TECHNICAL FIELD

This invention relates to processes for producing novel quinoline or quinazoline derivatives and their salts, which are useful as antiinflammatory agents, and to their intermediate compounds.

BACKGROUND ART

The present applicant previously filed patent applications on novel quinoline or quinazoline derivatives of value as antiinflammatory agents, particularly antiarthritic drugs (JP Application 206128/93 and JP Application 8232/94).

Referring to the technology for production of such novel quinoline or quinazoline derivatives and particularly in regard to the introduction of a 1,2,4-triazole group, this step was performed by the known reaction in the presence of a base.

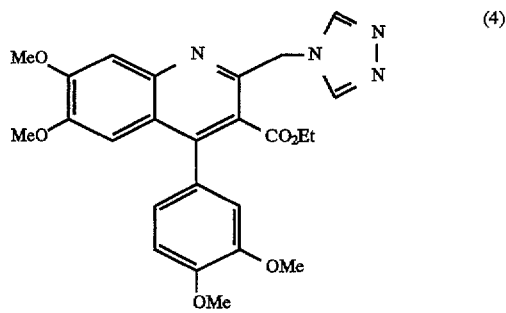

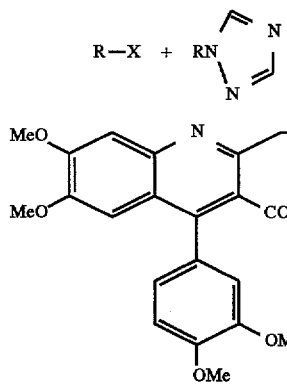

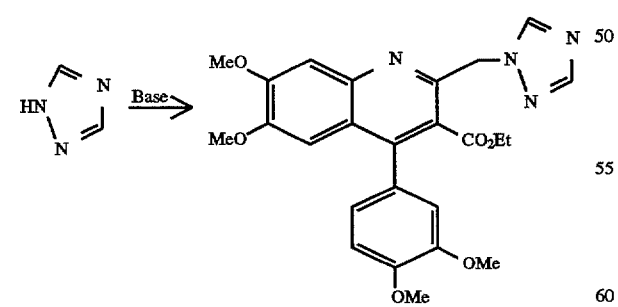

However, this reaction involved an isomerization reaction, Under basic conditions, of 1,2,4-triazole, thus giving rise to 1,3,4-triazole (4) as a byproduct in a proportion of 10–20%.

As a consequence, the yield was low and the necessary purification required a complicated procedure such as silica gel chromatography.

DISCLOSURE OF INVENTION

This invention is directed to:

1. A process for producing a compound of general formula (2)

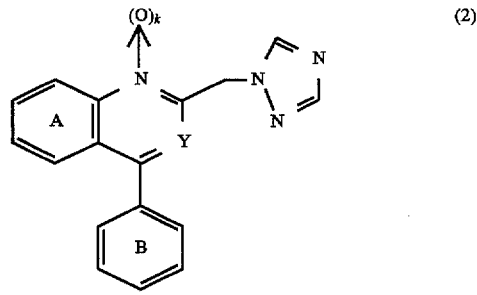

wherein Y represents a nitrogen atom or C-G in which G represents a carboxyl group which may optionally be esterified or amidated, an acyl group, a hydroxyalkyl group which may optionally be protected, or a halogen atom; ring A and ring B each may optionally be substituted; k represents 0 or 1; or a salt thereof, which comprises subjecting a compound of general formula (1)

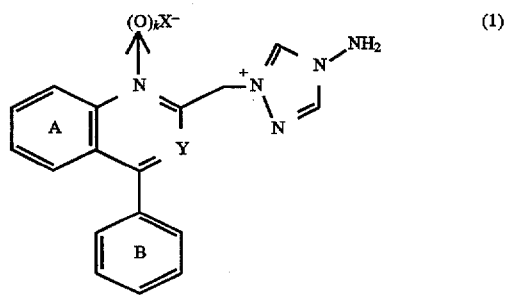

wherein Y, ring A, ring B, and k are respectively as defined above; X represents a leaving group; or a salt thereof to deamination reaction.

2. A process for producing a compound of general formula (1)

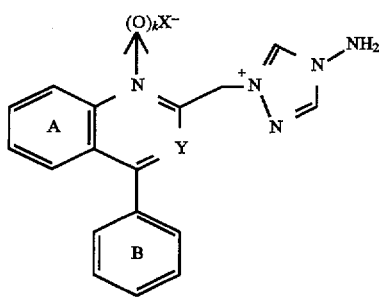

(1)

wherein X, Y, ring A, ring B, and k are respectively as defined above; or a salt thereof, which comprises reacting a compound of general formula (3)

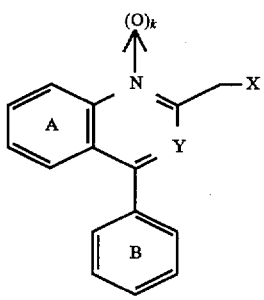

(3)

wherein X, Y, ring A, ring B and k are respectively as defined above; or a salt thereof with 4-amino-1,2,4-triazole.

3. A process for producing a compound of general formula (2)

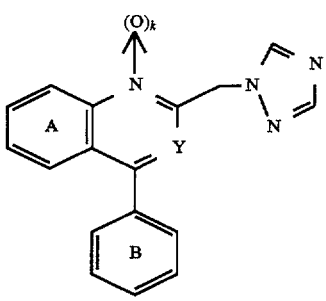

(2)

wherein Y, ring A, ring B, and k are respectively as defined above; or a salt thereof, which comprises reacting a compound of general formula (3)

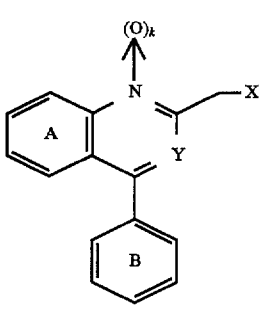

(3)

wherein X, Y, ring A, ring B and k are respectively as defined above; or a salt thereof with 4-amino-1,2,4-triazole to give a compound of general formula (1)

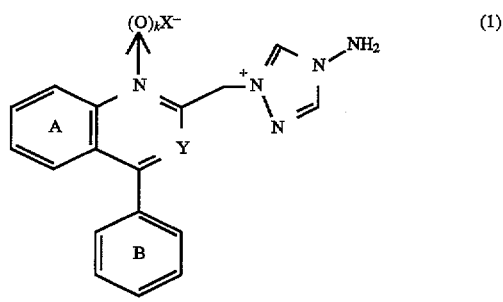

(1)

wherein X, Y, ring A, ring B, and k are respectively as defined above; or a salt thereof and subjecting the last-mentioned compound or salt thus obtained to deamination reaction.

4. The process according to the above items 1 or 3, wherein said deamination reaction is conducted using nitrous acid.

5. The process claimed in the above items 2 or 3, wherein X is a halogen atom.

6. The process claimed in the above items 1 or 3, wherein the compound of general formula (2) is ethyl 4-(3,4-dimethoxyphenyl)-6,7-dimethoxy-2-(1,2,4-triazol-1-ylmethyl)quinoline-3-carboxylate.

7. A compound of general formula (1)

(1)

wherein Y represents a nitrogen atom or C-G in which G represents a carboxyl group which may optionally be esterified or amidated, an acyl group, a hydroxyalkyl group which may optionally be protected, or a halogen atom; ring A and ring B each may optionally be substituted; k represents 0 or 1; X represents a leaving group; or a salt thereof.

8. The compound or salt of the above item 7, wherein Y represents C-G, where G represents $C_{1-6}$ alkyloxycarbonyl.

9. The compound or salt of the above item 8, wherein G represents ethoxycarbonyl.

10. The compound or salt of the above item 7, wherein ring A is substituted by two alkoxy groups which may be the same or different.

11. The compound or salt of the above item 7, wherein ring A is substituted by two methoxy groups.

12. The compound or salt of the above item 7, wherein ring B is substituted by two alkoxy groups which may be the same or different.

13. The compound or salt of the above item 7, wherein ring B is substituted by two methoxy groups.

14. The compound or salt thereof of general formula (1) of the above item 7, which is 4-amino-1-[4-(3,4-dimethoxyphenyl)-3-ethoxycarbonyl-6,7-dimethoxyquinolin-2-ylmethyl]-4H-1,2,4-triazolium bromide.

The various definitions relevant to the above general formulas and those falling within the purview of this invention, as well the preferred species thereof, are now presented below.

Referring to the above general formulas (1), (2) and (3), as they apply to quinoline derivatives in which Y represents C-G, the carboxyl group which may optionally be esterified, G, includes carboxyl, alkyloxycarbonyl and aralkyloxycarbonyl, among others.

The alkyl group of said alkyloxycarbonyl includes $C_{1-6}$ alkyl groups such as methyl, ethyl, propyl, isopropyl, butyl, isobutyl, sec-butyl, tert-butyl and so on, preferably methyl, ethyl and propyl, more preferably ethyl.

The aralkyl group of said aralkyloxycarbonyl is an alkyl group having an aryl group as a substituent (an arylalkyl group). The aryl group mentioned just above may for example be a phenyl or naphthyl group which may have substituents similar to those present on said ring A. The alkyl group is preferably a lower alkyl group of 1–6 carbon atoms. The preferred aralkyl group includes benzyl, phenethyl, 3-phenylpropyl, (1-naphthyl)methyl, (2-naphthyl)methyl, etc., and benzyl and phenethyl are particularly preferred.

Where G represents an amidated carboxyl group, this amidated carboxyl group can be represented by the formula —$CON(R^1)(R^2)$ (where $R^1$ and $R^2$ may be the same or different and each represents hydrogen, a hydrocarbon residue which may optionally be substituted or a heterocyclic group which may optionally be substituted).

The hydrocarbon group of said hydrocarbon residue which may optionally be substituted, $R^1$, $R^2$, includes aliphatic hydrocarbon groups, alicyclic hydrocarbon groups, alicycle-aliphatic hydrocarbon groups, aromatic carbocycle-aliphatic hydrocarbon groups, and aromatic hydrocarbon groups.

Among said aliphatic hydrocarbon groups may be mentioned saturated aliphatic hydrocarbon groups of 1–8 carbon atoms, such as methyl, ethyl, propyl, isopropyl, butyl, isobutyl, sec-butyl, t-butyl, pentyl, isopentyl, neopentyl, t-pentyl, hexyl, isohexyl, heptyl, octyl, etc. and unsaturated aliphatic hydrocarbon groups of 2–8 carbon atoms, such as ethenyl, 1-propenyl, 2-propenyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 3-hexenyl, 2,4-hexadienyl, 5-hexenyl, 1-heptenyl, 1-octenyl, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 3-hexynyl, 2,4-hexadiynyl, 5-hexynyl, 1-heptynyl, and 1-octynyl, among others.

Among said alicyclic hydrocarbon groups may be mentioned saturated alicyclic hydrocarbon groups of 3–7 carbon atoms, such as cyclopropyl, cyclobutyl, cyclopentyl, cyclohexyl, cycloheptyl, etc. and unsaturated alicyclic hydrocarbon groups of 5–7 carbon atoms, such as 1-cyclopentenyl, 2-cyclopentenyl, 3-cyclopentenyl, 1-cyclohexenyl, 2-cyclohexenyl, 3-cyclohexenyl, 1-cycloheptenyl, 2-cycloheptenyl, 3-cycloheptenyl, 2,4-cycloheptadienyl and so on.

Among said alicycle-aliphatic hydrocarbon residues may be mentioned those combinations of said alicyclic hydrocarbon groups with said aliphatic hydrocarbon residues which have a total of 4–9 carbon atoms, such as cyclopropylmethyl, cyclopropylethyl, cyclobutylmethyl, cyclopentylmethyl, 2-cyclopentenylmethyl, 3-cyclopentenylmethyl, cyclohexylmethyl, 2-cyclohexenylmethyl, 3-cyclohexenylmethyl, cyclohexylethyl, cyclohexylpropyl, cycloheptylmethyl, cycloheptylethyl and so on. Among said aromatic carbocycle-aliphatic hydrocarbon residues may be mentioned phenylalkyl groups of 7–9 carbon atoms, such as benzyl, phenetyl, 1-phenylethyl, 3-phenylpropyl, 2-phenylpropyl, 1-phenylpropyl, etc., and naphthylalkyl groups of 11–13 carbon atoms, such as α-naphthylmethyl, α-naphthylethyl, β-naphthylmethyl, β-naphthylethyl and so on.

Among said aromatic hydrocarbon residues may be mentioned phenyl, naphthyl (α-naphthyl, β-naphthyl) and so on.

The heterocyclic group of the optionally substituted heterocyclic group, represented by $R_1$, $R_2$, includes, among others, 5–7-membered heterocyclic groups containing one sulfur, nitorgen or oxygen atom, 5–6-membered heterocyclic groups containing 2–4 nitrogen atoms, 5–6-membered heterocyclic groups containing 1–2 nitrogen atoms and one sulfur or oxygen atom, and each of these heterocyclic groups may be fused to a 6-membered ring containing not more than 2 nitrogen atoms, a benzene ring, or a 5-membered ring containing one sulfur atom.

The heterocyclic group includes 2-pyridyl, 3-pyridyl, 4-pyridyl, 2-pyrimidinyl, 4-pyrimidinyl, 5-pyrimidinyl, 6-pyrimidinyl, 3-pyridazinyl, 4-pyridazinyl, 2-pyrazinyl, 2-pyrrolyl, 3-pyrrolyl, 2-imidazolyl, 4-imidazolyl, 5-imidazolyl, 3-pyrazolyl, 4-pyrazolyl, isothiazolyl, isooxazolyl, 2-thiazolyl, 4-thiazolyl, 5-thiazolyl, 2-oxazolyl, 4-oxazolyl, 5-oxazolyl, 1,2,4-triazol-3-yl, 1,3,4-triazol-2-yl, 1,2,3-triazol-4-yl, tetrazol-5-yl, benzimidazol-2-yl, indol-3-yl, benzopyrazol-3-yl, 1H-pyrrolo[2,3-b]pyrazin-2-yl, 1H-pyrrolo[2,3-b]pyridin-6-yl, 1H-imidazo[4,5-b]pyridin-2-yl, 1H-imidazo[4,5-c]pyridin-2-yl and 1H-imidazo[4,5-b]pyrazin-2-yl, among others.

The hydrocarbon residue and heterocyclic group, $R_1$, $R_2$ may each have 1–3 substituents in any substitutable positions of the ring. Among such substituents can be mentioned aliphatic acyclic hydrocarbon groups, alicyclic hydrocarbon groups, aryl groups, heteroaromatic groups, non-aromatic heterocyclic groups, halogen, nitro, amino which may be substituted, acyl which may be substituted, hydroxyl which may be substituted, thiol which may be substituted, and carboxyl which may be esterified.

The aliphatic acyclic hydrocarbon groups mentioned above as substituents on the hydrocarbon residue and heterocyclic group $R_1$, $R_2$ may be straight-chain or branched aliphatic hydrocarbon groups, such as alkyl, preferably of $C_{1-10}$ carbon atoms, alkenyl, particularly of $C_{1-10}$ carbon atoms, and alkynyl groups.

The preferred alkyl includes methyl, ethyl, propyl, isopropyl, butyl, isobutyl, sec-butyl, tert-butyl, pentyl, isopentyl, neopentyl, tert-pentyl, 1-ethylpropyl, hexyl, isohexyl, 1,1-dimethylbutyl, 2,2-dimethylbutyl, 3,3-dimethylbutyl, 2-ethylbutyl, hexyl, pentyl, octyl, nonyl and decyl, among others.

The preferred alkenyl includes vinyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl, among others.

The preferred alkynyl includes ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl, among others.

The alicyclic hydrocarbon group mentioned as a substituent on the hydrocarbon resiude and heterocyclic group $R_1$, $R_2$ is a saturated or unsaturated alicyclic hydrocarbon group such as cycloalkyl, cycloalkenyl, and cycloalkadienyl groups.

The preferred cycloalkyl includes cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl and bicyclo[4.3.1]decyl, among others.

The preferred cycloalkenyl incldues $C_{5-7}$ cycloalkenyl groups such as 2-cyclopenten-1-yl, 3-cyclopenten-1-yl, 2-cyclohexen-1-yl and 3-cyclohexen-1-yl, among others.

The prefererd cycloalkadienyl includes $C_{5-7}$ cycloalkadienyl groups such as 2,4-cyclopentadien-1-yl, 2,4-cyclohexadien-1-yl and 2,5-cyclohexadien-1-yl, among others.

The aryl group mentioned as a substituent on the hydrocarbon residue and heterocyclic group $R_1$, $R_2$ is a monocyclic or condensed polycyclic aromatic hydrocarbon group, such as phenyl, naphthyl, anthryl, phenanthryl, acenaphthylenyl and so on. Particularly prefered are phenyl, 1-naphthyl and 2-naphthyl.

The prefered heteroaromatic group mentioned as a substituent on the hydrocarbon residue and heterocyclic group $R_1$, $R_2$ incldues aromatic monocyclic heterocyclic groups such as furyl, thienyl, pyrrolyl, oxazolyl, isooxazoyl, thiazolyl, isothiazoyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, etc. and aromatic fused heterocyclic groups such as benzofuranyl, isobenzofuranyl, benzo[b]thienyl, indolyl, isoindolyl, 1H-indazolyl, benzimidazolyl, benzoxazolyl, 1,2-benzisoxazolyl, benzothiazolyl, 1,2-benzisothiazolyl, 1H-benzotriazolyl, quinolyl, isoquinolyl, cinnolinyl, quinazolinyl, quinoxalinyl, phthalazinyl, naphthiridinyl, purinyl, puteridinyl, carbazoyl, α-carbolinyl, β-carbolinyl, γ-carbolinyl, acryldinyl, phenoxazinyl, phenothiazinyl, phenazinyl, phenoxathiinyl, thianthrenyl, phenanthridinyl, phenanthrolinyl, indolidinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl and so on.

The preferred non-aromatic heterocyclic group mentioned as a substituent on the hydrocarbon residue and heterocyclic group $R_1$, $R_2$ includes oxiranyl, azetidinyl, oxetanyl, thietanyl, pyrrolidinyl, tetrahydrofuryl, thioranyl, piperidinyl, tetrahydropyranyl, morpholinyl, thiomorpholinyl, and piperazinyl, among other groups.

The halogen mentioned as a substituent on the hydrocarbon residue and heterocyclic group $R_1$, $R_2$ incldues fluorine, chlorine, bromine and iodine. Particularly preferred are fluorine and chlorine.

The amino group mentioned as a substituent on the hydrocarbon residue and heterocyclic group $R_1$, $R_2$ incldues amino and substituted amino as mono- or di-substituted by $C_{1-10}$ alkyl, $C_{2-10}$ alkenyl or aromatic groups (e.g. methylamino, dimethylamino, ethylamino, diethylamino, dibutylamino, diallylamino, cyclohexylamino, phenylamino, N-methyl-N-phenylamino, etc.).

The acyl group mentioned as a substituent on the hydrocarbon residue and heterocyclic group $R_1$, $R_2$ includes formyl and combinations of $C_{1-10}$ alkyl, $C_{2-10}$ alkenyl or aromatic groups with a carbonyl group (e.g. acetyl, propionyl, butyryl, isobutyryl, valeryl, isovaleryl, pivaloyl, hexanoyl, heptanoyl, octanoyl, cyclobutanoyl, cyclopentanoyl, cyclohexanoyl, cycloheptanoyl, crotonyl, 2-cyclohexenecarbonyl, benzoyl, nicotinoyl, etc.).

The optionally substituted hydroxyl group mentioned above as a substituent on the hydrocarbon residue and heterocyclic group $R_1$, $R_2$ incldues hydroxyl and subsituted hydroxyl, particularly as substituted by any of the groups which are usually employed as protective groups for hydroxyl function, such as alkoxy, alkenyloxy, aralkyloxy, acyloxy and even aryloxy.

The alkoxy mentioned above is preferably a $C_{1-10}$ alkoxy group (e.g. methoxy, ethoxy, propoxy, isopropoxy, butoxy, isobutoxy, sec-butoxy, tert-butoxy, pentoxy, isopentoxy, neopentoxy, hexyloxy, heptyloxy, nonyloxy, cyclobutoxy, cyclopentoxy, cyclohexyloxy, etc.).

The alkenyloxy includes groups of 2–10 carbon atoms, such as allyloxy, crotyloxy, 2-pentenyloxy, 3-hexenyloxy, 2-cyclopentenylmethoxy, and 2-cyclohexenylmethoxy, among others.

The aralkyloxy includes phenyl-$C_{1-4}$ alkyloxy (e.g. benzyloxy, phenethyloxy, etc.), among others.

The acyloxy is preferably a $C_{2-4}$ alkanoyloxy group (e.g. acetyloxy, propionyloxy, n-butyryloxy, isobutyryloxy, etc.). The aryloxy incldues phenoxy and 4-chlorophenoxy, among others.

The optionally substituted thiol group mentioned as a substituent on the hydrocarbon residue and heterocyclic group $R_1$, $R_2$ includes thiol and substituted thiol particularly as substituted by any of the groups which are commonly employed as protective groups for thiol function, such as alkylthio, aralkylthio, acylthio and so on.

The alkylthio mentioned above is preferably a $C_{1-10}$ alkylthio group (e.g. methylthio, ethylthio, propylthio, isopropylthio, butylthio, isobutylthio, sec-butylthio, tert-butylthio, pentylthio, isopentylthio, neopentylthio, hexylthio, heptylthio, nonylthio, cyclobutylthio, cyclopentylthio, cyclohexylthio, etc.).

The aralkylthio incldues phenyl-$C_{1-4}$ alkylthio groups (e.g. benzylthio, phenethylthio, etc.).

The acylthio is preferably a $C_{2-4}$ alkanoylthio group (e.g. acetylthio, propionylthio, n-butyrylthio, iso-butyrylthio, etc.).

The optionally esterified carboxyl group mentioned as a substituent on the hydrocarbon residue and heterocyclic group $R_1$, $R_2$ includes carboxy and combinations of carboxy with $C_{1-6}$ alkyl groups (such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentoxycarbonyl, hexyloxycarbonyl, etc.), combinations of carboxy with $C_{3-6}$ alkenyl groups (such as allyloxycarbonyl, crotyloxycarbonyl, 2-pentenyloxycarbonyl, 3-hexenyloxycarbonyl, etc.), and combinations of carboxy with aralkyl groups (such as benzyloxycarbonyl, phenethyloxycarbonyl, etc. and so on.

The substituents on the hydrocarbon residue and heterocyclic group $R_1$, $R_2$ may respectively have one or more, preferably 1–3, suitable substituents. Among such substituents may be mentioned lower alkyl, lower alkenyl, lower alkynyl, cycloalkyl, aryl, heteroaromatic groups, non-aromatic heterocyclic groups, aralkyl, amino, mono-N-substituted amino, di-N,N-substituted amino, amidino, acyl, carbamoyl, mono-N-substituted carbamoyl, di-N,N-substituted carbamoyl, sulfamoyl, mono-N-substituted sulfamoyl, di-N,N-substituted sulfamoyl, carboxyl, lower alkoxycarbonyl, hydroxyl, lower alkoxy, lower alkenyloxy, cycloalkyloxy, lower alkylthio, aralkylthio, arylthio, sulfo, cyano, azido, halogen, nitro, nitroso, etc. As exemplary species of the substituents, those mentioned for the substituents on the hydrocarbon residue and heterocyclic group $R_1$, $R_2$ can be mentioned.

Where G represents acyl, the acyl group can be represented by the formula —CO—$R^3$ ($R^3$ is $C_{1-5}$ alkyl or aryl). The $C_{1-5}$ alkyl for $R^3$ includes methyl, ethyl, isopropyl, butyl, isobutyl, sec-butyl, tert-butyl, pentyl, isopentyl, neopentyl, tert-pentyl and 1-ethylpropyl, among others. The aryl for $R^3$ means a monocyclic or condensed polycyclic aromatic hydrocarbon group, including such preferred species as phenyl, naphthyl and anthryl.

Where G represents hydroxyalkyl, the hydroxyalkyl group can be represented by the formula —$CH_2OH$ or —CH(OH)—$R^3$ ($R^3$ has the same meaning as defined above).

Where G represents protected hydroxyalkyl, the protected hydroxyalkyl group means —$CH_2OCOR^4$ or —CH(OCOR$^4$)—$R^3$ ($R^3$ has the same meaning as defined above; $R^4$ means an alkyl, aralkyl or aryl group which may optionally be substituted). The alkyl $R^4$ is a $C_{1-6}$ alkyl group such as methyl, ethyl, propyl, isopropyl, butyl, isobutyl, sec-butyl, tert-butyl, etc. The aralkyl for $R^4$ is an aryl-substituted alkyl group, e.g. a $C_{1-4}$ alkyl group, (arylalkyl group). The aryl group mentioned just above includes phenyl and naphthyl, among others, while the aralkyl incldues benzyl, phenethyl, 3-phenylpropyl, (1-naphthyl)methyl and (2-naphthyl)methyl, among others. The aryl $R^4$ may for example be phenyl or naphthyl.

Where G represents a halogen atom, the halogen may be chlorine, bromine, iodine or fluorine and preferably is chlorine or bromine.

Referring, further, to general formulas (1), (2) and (3), ring A and ring B may have substituents. Among such substituents are halogen, nitro, alkyl which may be substituted, hydroxyl which may be substituted, thiol which may be substituted, amino which may be substituted, acyl which may be substituted, carboxyl which may be esterified, and aromatic groups which may be substituted.

The halogen atom as a substituent on ring A and ring B includes fluorine, chlorine, bromine and iodine, and fluorine and chlorine are particularly preferred.

The alkyl which may be substituted, as a substituent that may be present on ring A and ring B includes $C_{1-10}$ alkyl groups which may be straight-chain, branched or cyclic, such as methyl, ethyl, propyl, isopropyl, butyl, isobutyl, sec-butyl, tert-butyl, pentyl, isopentyl, neopentyl, hexyl, heptyl, octyl, nonyl, decyl, cyclopropyl, cyclobutyl, cyclopentyl, cyclohexyl and cycloheptyl, among others.

The optionally substituted hydroxyl as a substituent on ring A and ring B incldues hydroxyl and substituted hydroxyl particularly as substituted by a hydroxy-protecting group, such as alkoxy, alkenyloxy, aralkyloxy, acyloxy and aryloxy. The alkoxy mentioned just above is preferably a $C_{1-10}$ alkoxy group (e.g. methoxy, ethoxy, propoxy, isopropoxy, butoxy, isobutoxy, sec-butoxy, tert-butoxy, pentoxy, isopentoxy, neopentoxy, hexyloxy, heptyloxy, nonyloxy, cyclobutoxy, cyclopentoxy, cyclohexyloxy, etc.). The alkenyloxy mentioned above includes $C_{2-10}$ groups such as allyloxy, crotyloxy, 2-pentenyloxy, 3-hexenyloxy, 2-cyclopentenylmethoxy and 2-cyclohexenylmethoxy, among others. The aralkyloxy inlcudes phenyl-$C_{1-4}$ alkyloxy groups (e.g. benzyloxy, phenethyloxy, etc.). The acyloxy is preferably a $C_{2-4}$ alkanoyloxy group (e.g. acetyloxy, propionyloxy, n-butyryloxy, isobutyryloxy, etc.). The aryloxy mentioned above includes phenoxy and 4-chlorophenoxy, among others.

The optionally substituted thiol as a substituent on ring A and ring B incldues thiol and substituted thiol particularly as substituted by any of the substituents commonly used as protective groups for thiol function, such as alkylthio, aralkylthio, acylthio and others. The alkylthio mentioned just above is preferably a $C_{1-10}$ alkylthio group (e.g. methylthio, ethylthio, propylthio, isopropylthio, butylthio, isobutylthio, sec-butylthio, tert-butylthio, pentylthio, isopentylthio, neopentylthio, hexylthio, heptylthio, nonylthio, cyclobutylthio, cyclopentylthio, cyclohexylthio, etc.). The aralkylthio includes phenyl-$C_{1-4}$ alkylthio groups (e.g. benzylthio, phenethylthio, etc.). The acylthio is preferably a $C_{2-4}$ alkanoylthio group (e.g. acetylthio, propionylthio, n-butyrylthio, isobutyrylthio, etc.).

The optionally substituted amino group as a substituent on ring A and ring B incldues substituted amino as substituted by one or two $C_{1-10}$ alkyl, $C_{2-10}$ alkenyl, aromatic or acyl groups (e.g. methylamino, dimethylamino, ethylamino, diethylamino, dibutylamino, diallylamino, cyclohexylamino, phenylamino, N-methyl-N-phenylamino, acetylamino, propionylamino, benzoylamino, etc.).

The optionally substituted acyl group as a substituent on ring A and ring B includes formyl and combinations of $C_{1-10}$ alkyl, $C_{2-10}$ alkenyl or aromatic groups with carbonyl (e.g. acetyl, propionyl, butyryl, isobutyryl, valeryl, isovaleryl, pivaloyl, hexanoyl, heptanoyl, octanoyl, cyclobutanoyl, cyclopentanoyl, cyclohexanoyl, cycloheptanoyl, crotonyl, 2-cyclohexenecarbonyl, benzoyl, nicotinoyl, etc.)

The optionally esterified carboxyl as a substituent on ring A and ring B includes carboxyl, alkyloxycarbonyl and aralkyloxycarbonyl. The alkyl moiety of said alkyloxycarbonyl includes $C_{1-6}$ alkyl groups such as methyl, ethyl, propyl, isopropyl, butyl, isobutyl, sec-butyl and t-butyl, among others.

The aralkyl moiety of said aralkyloxycarbonyl is an arylalkyl group, and its aryl moiety may for example be phenyl or naphthyl, which may have substituents similar to those mentioned for the aryl group for said ring R. The alkyl group is preferably a lower ($C_{1-6}$) alkyl group. The aralkyl includes benzyl, phenethyl, 3-phenylpropyl, (1-naphthyl)methyl, (2-naphthyl)methyl, etc. and is preferably benzyl or phenethyl.

The optionally substituted aromatic group as a substituent on ring A and ring B includes not only $C_{6-14}$ aromatic hydrocarbon residues, such as phenyl, naphthyl, anthryl, etc., but also heteroaromatic residues, such as pyridyl, furyl, thienyl, imidazolyl and thiazolyl, among others.

These substituents on ring A and ring B may be situated in any optional positions of the respective rings. The substituent on ring A is preferably situated in the 6- and/or 7-position of the quinoline ring of ring A. The substituent on ring B is preferably situated in the 3- and/or 4-position of ring B. These substituents may be the same or different, and may number 1–4, preferably 1–2. Where the substituents on ring A or ring B are adjacent to each other, the adjacent substituent groups may combine with each other to form a ring represented by the formula —$(CH_2)_m$— or —O—$(CH_2)_l$—O— [where m represents a whole number of 3–5, l represents a whole number of 1–3] and such ring includes a 5–7-membered ring formed together with the carbon atoms of the benzene ring.

The preferred case in which the substituent on ring A has substituent groups includes, among others, the case in which the 6, 7-positions of the quinoline ring of ring A are substituted by a methylenedioxy group; the case in which ring A is substituted by the same or different alkoxy groups, particularly by methoxy; and the case in which ring A is di-substituted by the same or different alkoxy groups in the 6- and 7-positions of the quinoline ring, particularly methoxy in the 6- and 7-positions of the quinoline ring, among other cases.

The preferred case in which the substituent on ring B has substituents includes the case in which the substituent on ring B is methylenedioxy; the case in which the substituent on ring B is alkoxy, especially methoxy; the case in which ring B is di-substituted by the same or different alkoxy groups, particularly by methoxy groups; the case in which the 3- or 4-position of ring B is substituted by methoxy; and the case in which ring B is di-substituted by methoxy groups in 3- and 4-positions, among other cases.

Referring, further, to general formulas (1), (2) and (3), Y is preferably C-G, wherein G is preferably $C_{1-6}$ alkyloxycarbonyl and most preferably ethoxycarbonyl.

In the general formulas (1), (2) and (3), k is preferably 0.

Prefered example of the compound or a salt thereof of the formula (1) is 4-amino-1-[4-(3,4-dimethoxyphenyl)-3-ethoxycarbonyl-6,7-dimethoxyquinolin-2-ylmethyl]-4H-1,2,4-triazolium bromide.

Prefered example of the compound or a salt thereof of the formula (2) is ethyl 4-(3,4-dimethoxyphenyl)-6,7-dimethoxy-2-(1,2,4-triazol-1-ylmethyl)quinoline-3-carboxylate.

The leaving group in general formula (3) includes halogen, e.g. chlorine, bromine, iodine and fluorine; $C_{1-6}$ alkylsulfonyloxy groups which may be substituted by 1–3 halogen atoms such as chlorine, bromine, fluorine, etc., e.g. methanesulfonyloxy, ethanesulfonyloxy, butanesulfonyloxy, trifluoromethanesulfonyloxy, etc.; $C_{6-10}$ arylsulfonyloxy groups which may be substituted by 1–4 halogen atoms such as chlorine, bromide, fluorine, etc., e.g. benzenesulfonyloxy, p-toluenesulfonyloxy, p-bromobenzenesulfonyloxy, methylenesulfonyloxy, etc.; $C_{1-6}$ acyloxy groups which may be substituted by 1–3 halogen atoms such as chlorine, bromine, fluorine, etc., e.g. acetyloxy, propionyloxy, trifluoroacetyloxy, etc.; $C_{1-6}$ alkylsulfinyl groups, e.g. methylsulfinyl, ethylsulfinyl, etc.; and $C_{1-6}$ alkylsulfonyl groups, e.g. methylsulfonyl, ethylsulfonyl, etc.

Preferably, a halogen atom is used.

The salts of said compounds of general formula (1), (2) and (3) for use in this invention are preferably pharmaceutically acceptable salts, thus including salts with inorganic bases, salts with organic bases, salts with inorganic acids, salts with organic acids, and salts with either basic or acidic amino acids. The preferred inorganic basic salt includes but is not limited to alkali metal salts such as sodium salt, potassium salt, etc.; alkaline earth metal salts such as calcium salt, magnesium salt, etc.; aluminum salt and ammonium salt, among others. The preferred organic base salt includes salts with trimethylamine, triethylamine, pyridine, picoline, ethanolamine, diethanolamine, triethanolamine, dicyclohexylamine, N,N'-dibenzylethylenediamine, etc. Among the preferred salts with inorganic acids are salts with hydrochloric acid, hydrobromic acid, nitric acid, sulfuric acid, phosphoric acid, etc. Among the preferred salts with organic acids are salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc. The preferred salt with a basic amino acid includes salts with arginine, lysine, ornithine, etc. The preferred salt with an acidic amino acid includes salts with aspartic acid, glutamic acid, etc.

Deamination of the compound of the formula (I) in accordance with this invention can be carried out by known techniques such as oxidative deamination with $I_2O_4$, $(CH_3CO_2)_4Pb$, $HgO$, $KMnO_4$, $NaIO_4$ or the like, hydrogenation with Raney nickel, deamination under strongly acidic conditions, etc.

Preferably, deamination with nitrous acid is employed. Nitrous acid is usually prepared from sodium nitrite or potassium nitrite and hydrochloric acid. Deamination reaction with nitrous acid can be typically carried out by a process which comprises adding 1–10 molar equivalents, preferably 1–5 molar equivalents, of sodium nitrite or potassium nitrite and 2–20 molar equivalents, preferably 2–6 molar equivalents, of hydrochloric acid to each mol of the compound of general formula 1 and stirring the mixture at a reaction temperature of −10° C.–50° C., preferably −10° C.–30° C., for about 10 min.–24 hrs, preferably 30 min.–5 hrs. Sodium nitrite is preferably used in the form of an aqueous solution, the normality of which may be about 0.5–5.5.

The reaction may be conducted in the presence of a solvent.

The solvent that can be used includes water, alcohols such as methanol, ethanol, n-propanol, isopropyl alcohol, etc., aromatic hydrocarbons such as benzene, toluene, xylene, etc., halogenated hydrocarbons such as dichloromethane, chloroform, etc., ethers such as diethyl ether, tetrahydrofuran, dioxane, etc., ketones such as acetone, methyl ethyl ketone, etc., nitriles such as acetonitrile, sulfoxides such as dimethyl sulfoxide, acid amides such as N,N-dimethylformamide, esters such as ethyl acetate, and carboxylic acids such as acetic acid, propionic acid, etc., among others. These solvents can be used independently or, where necessary, in a combination of two or more species in a ratio of, for example, 1:1–1:10.

After completion of the reaction, the reaction system is neutralized with an aqueous solution of sodium hydroxide or potassium hydroxide and the resulting crystalline precipitate is recovered by filtration, whereby the compound of general formula (2) can be obtained.

The compound of general formula (1) for use in this invention can be synthesized by reacting a compound of general formula (3) with 4-amino-1,2,4-triazole.

This reaction can be carried out by, for example, adding 1–10 molar equivalents, preferably 1–2 molar equivalents, of 4-amino-1,2,4-triazole to one molar equivalent of the compound of general formula (3) and allowing them to react at a temperature of 50°–160° C., preferably 60°–80° C., for 0.2–15 hours, preferably 0.5–5 hours.

This reaction is carried out in a suitable solvent. The solvent can be any of the solvents mentioned above. Particularly with a polar solvent such as N,N-dimethylformamide or dimethyl sulfoxide, the object compound can be obtained in a higher yield in a shorter reaction time as compared with any other solvent. The amount of the solvent can be such that the concentration of the compound of general formula (3) will be 0.1–3.0 molar, preferably 0.5–1.0 molar.

Where the leaving group X of the compound of general formula (3) is a chlorine atom, this reaction can be expedited by adding an alkali metal bromide or an alkali metal iodide, e.g. potassium bromide, sodium bromide, potassium iodide or sodium iodide, beforehand so as to replace the chlorine atom, for said leaving group X, with a bromine atom or an iodine atom. The level of addition of the alkali metal bromide or alkali metal iodide may for example be 0.5–10 mols, preferably 1–5 mols, per mol of the compound of general formula (3), and it can be added prior to or simultaneously with addition of 4-amino-1,2,4-triazole.

The compound of general formula (1) which separates out on completion of the reaction can be subjected to the deamination reaction without prior isolation. Where necessary, it can be isolated and purified by known procedures such as concentration, concentration under reduced pressure, distillation, fractional distillation, solvent extraction, pH adjustment, redistribution, chromatography, crystallization and recrystallization.

The compound of general formula (3) can be produced by, for example, the following processes.

Process A

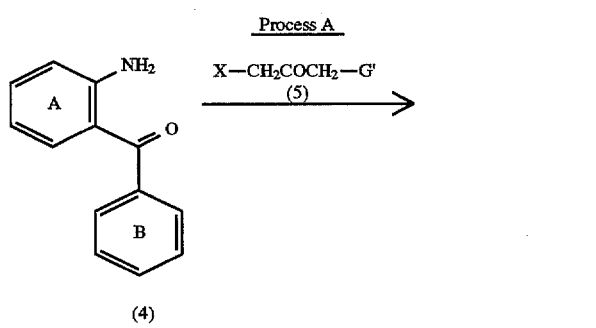

(4)

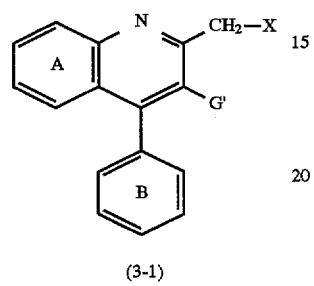

(3-1)

[wherein G' represents an esterified carboxyl group; the other symbols have the meanings defined hereinbefore]. The esterified carboxyl group G' may be selected from among those species mentioned for the esterified carboxyl group G.

In this process, 2-aminobenzophenone derivative (4) is reacted with compound (5) in the presence of an acid to prepare compound (3-1). The reaction between (4) and (5) is conducted in a suitable solvent. The solvent that can be used includes aromatic hydrocarbons such as benzene, toluene, xylene, etc., ethers such as dioxane, tetrahydrofuran, dimethoxyethane, etc., N,N-dimethylformaide, dimethyl sulfoxide, chloroform, dichloromethane, 1,2-dichloroethane, 1,1,2,2-tetrachloroethane, and acetic acid, among others. The reaction between (4) and (5) is conducted in the presence of a suitable acid such as a Lewis acid, e.g. aluminum chloride, zinc chloride, etc., sulfuric acid or trifluoroacetic acid. The amount of the acid relative to compound (4) is about 0.01-2.0 molar equivalents, preferably about 0.05-0.5 molar equivalents. This reaction is carried out at a temperature of generally 20° C.–200° C. and preferably about 30° C.–150° C. The reaction time is 0.5–20 hours, preferably 1-10 hours.

The compound (3-1) thus obtained can be isolated and purified by conventional separation and purification procedures such as concentration, concentration under reduced pressure, solvent extraction, crystallization, recrystallization, redistribution, chromatography, etc.

Process B

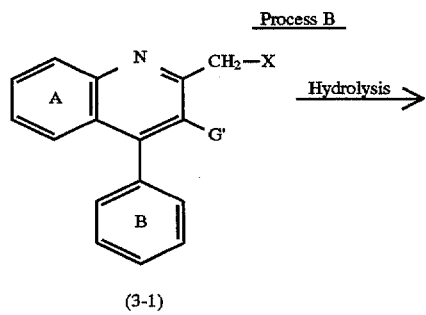

(3-1)

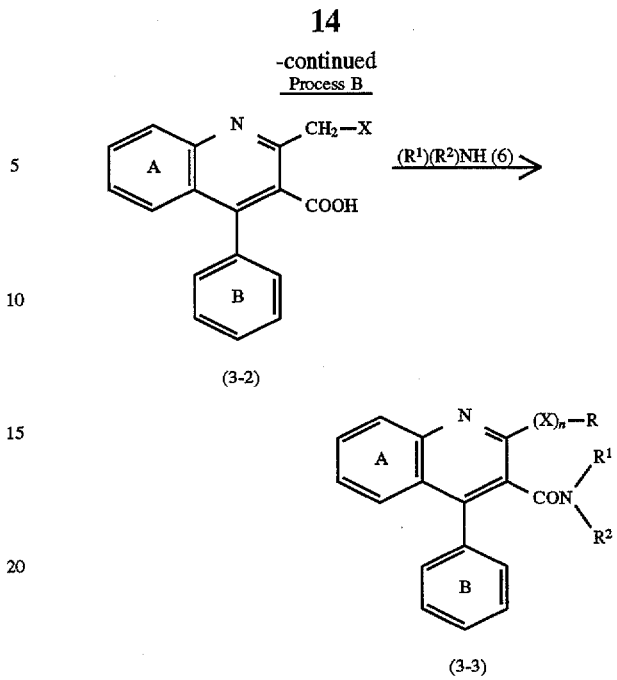

[wherein the respective symbols have the meanings defined hereinbefore]

In this process, quinoline ester derivative (3-1) is hydrolyzed to carboxylic acid derivative (3-2). This hydrolysis reaction is conducted in the conventional manner, viz. in a solvent in the presence of an acid or a base. The solvent that can be used may for example be a mixture of water with an alcohol such as methanol or ethanol, an ether such as tetrahydrofuran or dioxane, N,N-dimethylformamide, dimethyl sulfoxide or acetone. The base may for example be potassium carbonate, sodium carbonate, sodium methoxide, sodium ethoxide, potassium tert-butoxide, sodium hydroxide, potassium hydroxide or lithium hydroxide. The acid may for example be hydrochloric acid, sulfuric acid, acetic acid or hydrobromic acid. Such acid or base is preferably used in excess (base: 1.2–10 equivalents, acid: 2–50 equivalents) relative to compound (3-1). This reaction is carried out generally at −20° C.–150° C. and preferably about −10° C.–100° C.

The compound (3-2) is then subjected to amidation reaction to give (3-3). This amidation reaction is carried out using compound (3-2) and compound (6). The condensation reaction between (3-2) and (6) can be carried out by the conventional reaction technology for peptide synthesis. Thus, the peptide synthesis reaction can be carried out by any of the known processes such as the prosesses described in M. Bodansky and M. A. Ondetti: Peptide Synthesis, Interscience, New York, 1966; F. M. Finn and K. Hofmann: The Proteins, Vol.2, H. Nenrath & R. L. Hill (ad.), Academic Press, Inc., New York, 1976; and N. Izumiya et al.: Peptide Gosei-no-Kiso-to-Jikken, Maruzen, 1985, or specifically, the azide process, chloride process, acid anhydride process, mixed acid anhydride process, DCC process, activated ester process, Woodwards reagent K process, carbonyldiimidazole process, redox process, DCC/HONB process, and further the process using DEPC (diethyl cyanophosphate). This condensation reaction can be carried out in a solvent. The solvent may for example be anhydrous or hydrous dimethylformamide, dimethyl sulfoxide, pyridine, chloroform, dichloromethane, tetrahydrofuran or acetonitrile, or a suitable mixture thereof. The reaction temperature is generally about −20° C.–50° C. and preferably −10° C.–30° C. The reaction time is generally 1–100 hours and preferably 2–40 hours.

The quinoline derivatives (3-2) and (3-3) obtained by the above procedures can be respectively isolated and purified by known separation and purification procedures such as concentration, concentration under reduced pressure, solvent extraction, crystallization, recrystallization, redistribution, chromatography and so on.

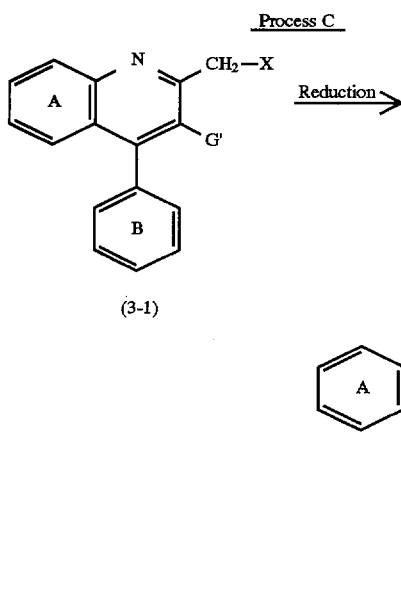

[wherein the respective symbols have the meanings defined hereinbefore]

In this process, compound (3-1) is reduced to the corresponding alcohol (3-4). This reduction reaction can be carried out by the per se known processes. Thus, for example, reduction with a metal hydride, reduction with a metal complex hydride compound, reduction with a diborane or a substituted borane, and catalytic hydrogenation can be mentioned. Thus, this reaction is carried out by treating compound (3-1) with a reducing agent. The reducing agent that can be used includes alkali metal borohydrides (e.g. sodium borohydride, lithium borohydride, etc.), metal complex hydride compounds such as lithium aluminum hydride, metal hydrides such as sodium hydride, organotin compounds (e.g. triphenyltin hydride), and a metal or a metal salt, e.g. nickel compounds, zinc compounds, etc., catalytic reduction systems using hydrogen and a transition metal, e.g. palladium, platinum, rhodium, etc., and a diborane or the like, among others.

This reaction is conducted in an organic solvent that does not adversely affect the reaction. Thus, as the solvent, aromatic hydrocarbons such as benzene, toluene, xylene, etc., halogenated hydrocarbons such as chloroform, carbon tetrachloride, dichloromethane, 1,2-dichloroethane, 1,1,2,2-tetrachloroethane, etc., ethers such as diethyl ether, tetrahydrofuran, dioxane, etc., alcohols such as methanol, ethanol, propanol, isopropyl alcohol, 2-methoxyethanol, etc., amides such as N,N-dimethylformamide etc., and mixtures of such solvents can be selectively employed according to the type of reducing agent. The reaction temperature is −20° C.–150° C., preferably 0° C.–100° C., and the reaction time is about 1–24 hours.

The quinoline derivative (3-4) thus obtained can be isolated and purified by known separation and purification procedures such as concentration, concentration under reduced pressure, solvent extraction, crystallization, recrystallization, redistribution, and chromatography.

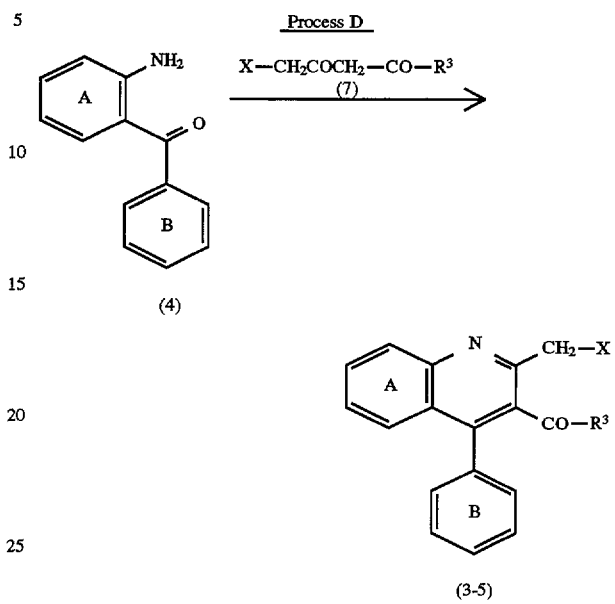

[wherein the respective symbols have the meanings defined hereinbefore]

In this process, 2-aminobenzophenone derivative (4) is reacted with (7) in the presence of an acid to give (3-5). The reaction between (4) and (7) is conducted in a suitable solvent. The solvent that can be used includes aromatic hydrocarbons such as benzene, toluene, xylene, etc., ethers such as dioxane, tetrahydrofuran, dimethoxyethane, etc., N,N-dimethylformamide, dimethyl sulfoxide, chloroform, dichloromethane, 1,2-dichloroethane, 1,1,2,2-tetrachloroethane and acetic acid, among others. The reaction between (4) and (7) is conducted in the presence of a suitable acid such as a Lewis acid, e.g. aluminum chloride, zinc chloride, etc., sulfuric acid, trifluoroacetic acid or the like. The proportion of said acid is about 0.01–2.0 molar equivalents, preferably about 0.05–0.5 molar equivalents, based on compound (4). This reaction is carried out generally at 20° C.–200° C. and preferably at about 30° C.–150° C. The reaction time is 0.5–20 hours, preferably 1–10 hours.

The compound (3-5) thus obtained can be isolated and purified by known separation and isolation procedures such as concentration, concentration under reduced pressure, solvent extraction, crystallization, recrystallization, redistribution and chromatography.

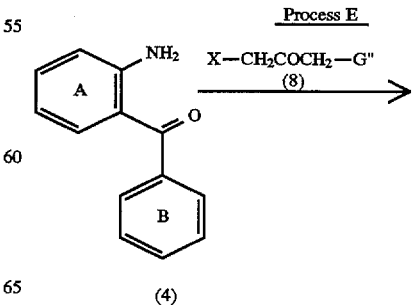

-continued
Process E

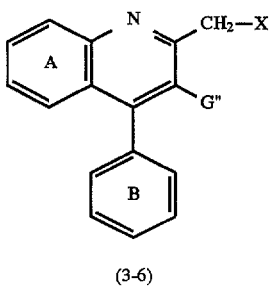

(3-6)

[wherein G" represents an esterified carboxyl group; the other symbols have the meanings defined hereinbefore]

The esterified carboxyl group G" that can be used includes the species mentioned for the esterified carboxyl group.

In this process, 2-aminobenzophenone derivative (4) is reacted with (8) in the presence of an acid to give (3-6). The reaction between (4) and (8) is carried out in a suitable solvent. The solvent that can be used includes aromatic hydrocarbons such as benzene, toluene, xylene, etc., ethers such as dioxane, tetrahydrofuran, dimethoxyethane, etc., N,N-dimethylformamide, dimethyl sulfoxide, chloroform, dichloromethane, 1,2-dichloroethane, 1,1,2,2-tetrachloroethane and acetic acid, among other solvents. The reaction between (4) and (8) is carried out in the presence of a suitable acid such as a Lewis acid, e.g. aluminum chloride, zinc chloride, etc., sulfuric acid, trifluoroacetic acid or the like. The proportion of the acid relative to compound (4) is about 0.01–2.0 molar equivalents, preferably about 0.05–0.5 molar equivalents. This reaction is carried out generally at 20° C.–200° C. and preferably at about 30° C.–150° C. The reaction time is 0.5–20 hours, preferably 1–10 hours.

The compound (3-6) thus obtained can be isolated and purified by known separation and purification procedures such as concentration, concentration under reduced pressure, solvent extraction, crystallization, recrystallization, redistribution and chromatography.

Process F

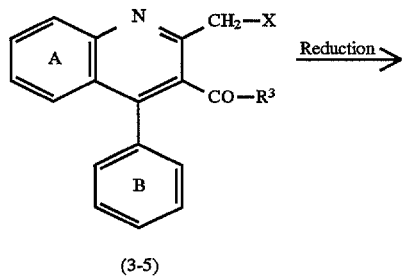

(3-5)

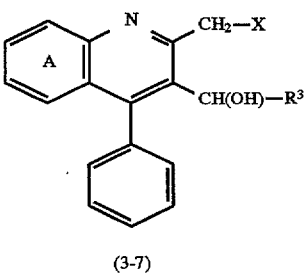

(3-7)

[wherein the respective symbols have the meanings defined hereinbefore]

In this process, compound (3-5) is reduced to alcohol (3-7). This reduction reaction can be carried out by per se known processes. Thus, for example, reduction with a metal hydride, reduction with a metal complex hydride compound, reduction with a diborane or a substituted borane, and catalytic hydrogenation can be employed. Thus, this reaction proceeds as compound (3-5) is treated with a reducing agent. The reducing agent includes alkali metal borohydrides (e.g. sodium borohydride, lithium borohydride, etc.), aluminum complex hydride compounds such as lithium aluminum hydride, metal hydrides such as sodium hydride, organotin compounds (e.g. triphenyltin hydride), various metals, metal salts such as nickel or zinc compounds, and catalytic reduction systems using hydrogen and transition metals such as palladium, platinum, rhodium, etc., and a diborane or the like, among others. This reaction is conducted in an organic solvent that does not adversely affect the reaction. Thus, as the solvent, aromatic hydrocarbons such as benzene, toluene, xylene, etc., halogenated hydrocarbons such as chloroform, carbon tetrachloride, dichloromethane, 1,2-dichloroethane, 1,1,2,2-tetrachloroethane, etc., ethers such as diethyl ether, tetrahydrofuran, dioxane, etc., alcohols such as methanol, ethanol, propanol, isopropyl alcohol, 2-methoxyethanol, etc., amides such as N,N-dimethylformamide etc., and mixtures of such solvents can be selectively employed according to the type of reducing agent. The reaction temperature is –20° C.–150° C., preferably 0° C.–100° C., and the reaction time is about 1–24 hours.

The compound (3-7) thus obtained can be isolated and purified by known separation and purification procedures such as concentration, concentration under reduced pressure, solvent extraction, crystallization, recrystallization, redistribution, and chromatography.

Process G (3-7) $\xrightarrow{R^4-COOH\ (9)}$ 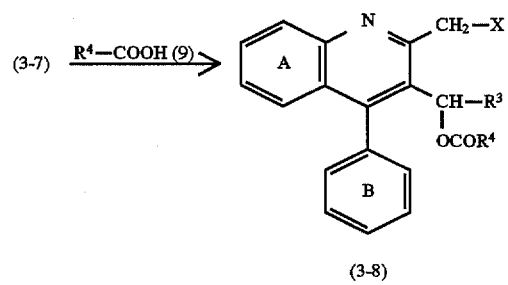

(3-8)

(3-4) $\xrightarrow{R^4-COOH\ (9)}$ 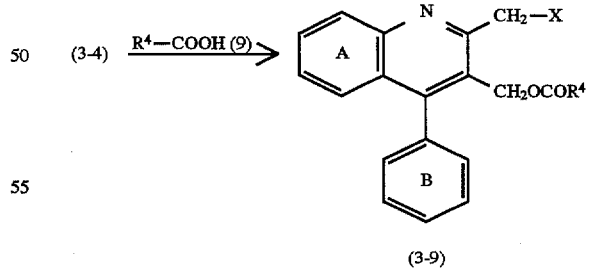

(3-9)

[wherein the respective symbols have the meanings defined hereinbefore]

In this process, the technology of acylating alcohol derivatives is utilized to convert (3-7) to (3-8), and (3-4) to (3-9).

In this process, compound (9) or a reactive derivative of its carboxyl group is reacted with (3-7) or (3-4) to give (3-8) or (3-9) as the case may be. The preferred reactive derivative of compound (9) at its carboxyl function includes acid halides, acid anhydrides, activated amides and activated esters. The specific preferred reactive derivative includes the acid chloride; the acid azide; the mixed acid anhydride with a substituted phosphoric acid, e.g. dialkylphosphoric acid, phenylphosphoric acid, diphenylphosphoric acid, dibenzylphosphoric acid, halophosphoric acid, etc., a dialkylphosphorous acid, sulfurous acid, thiosulfuric acid, sulfuric acid, a sulfonic acid, e.g. methanesulfonic acid, an aliphatic carboxylic acid, e.g. acetic acid, propionic acid, butyric acid, isobutyric acid, pivalic acid, pentanoic acid, isopentanoic acid, trichloroacetic acid, etc., or an aromatic carboxylic acid such as benzoic acid; the symmetric acid anhydride; the activated amide with imidazole, 4-substituted imidazole, dimethylpyrazole, triazole, tetrazole or the like; activated esters such as the cyanomethyl ester, methoxymethyl ester, dimethyliminomethyl ester, vinyl ester, propargyl ester, p-nitrophenyl ester, trichlorophenyl ester, pentachlorophenyl ester, mesylphenyl ester, phenylazophenyl ester, phenylthio ester, p-nitrophenyl ester, p-cresylthio ester, carboxymethylthio ester, pyranyl ester, pyridyl ester, piperidyl ester, 8-quinolylthio ester, etc., and esters with N-hydroxy compounds such as N,N-dimethylhydroxylamine, 1-hydroxy-2-(1H)-pyridone, N-hydroxysuccinimide, N-hydroxyphthalimide, 1-hydroxy-1H-benzotriazole, etc., among other derivatives. These reactive derivatives can be selectively employed. The reaction is generally conducted in the common solvent such as water, an alcohol, e.g. methanol, ethanol, etc., acetone, dioxane, acetonitrile, chloroform, methylene chloride, ethylene chloride, tetrahydrofuran, ethyl acetate, N,N-dimethylformamide, pyridine, etc. but the reaction can be carried out in any other organic solvent that does not interfere with its progress. The common solvent mentioned above can be used in admixture with water. When compound (9) is used in the form of free acid or a salt thereof in this reaction, the reaction is preferably carried out in the presence of an ordinary condensing agent such as N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, N,N'-carbonylbis(2-methylimidazole), pentamethyleneketene-N-cyclohexylimine, diphenylketene-N-cyclohexylimine, ethoxyacetylene, 1-alkoxy-1-chloroethylenes, trialkyl phosphites, ethyl polyphosphate, isopropyl polyphosphate, phosphorus oxychloride, diphenylphosphorylazide, thionyl chloride, oxalyl chloride, lower alkyl haloformates such as ethyl chloroformate, isopropyl chloroformate, etc., triphenylphosphine, 2-ethyl-7-hydroxybenzisoxazolium salts, 2-ethyl-5-(m-sulfophenyl)isoxazolium hydroxide inner salt, N-hydroxybenzotriazole, 1-(p-chlorobenzenesulfonyloxy)-6-chloro-1H-benzotriazole, Virsmier's reagents prepared by reacting N,N'-dimethylformamide with thionyl chloride, phosgene, trichloromethyl chloroformate, phosphorus oxychloride, etc. The reaction may also be conducted in the presence of an inorganic or organic base such as alkali metal bicarbonates, tri(lower)alkylamines, pyridine, N-(lower) alkylmorpholines, N,N-di(lower)alkylbenzylamines and so on. The reaction temperature is not critical but the reaction is conducted generally under cooling through warming temperatures.

The quinoline derivatives (3-7) and (3-8) obtained in the above manner can be respectively isolated and purified by known separation and isolation procedures such as concentration, concentration under reduced pressure, solvent extraction, crystallization, recrystallization, redistribution, and chromatography.

According to the production technology of this invention, new quinoline or quinazoline derivatives and their salts which are of value as antiinflammatory agents can be produced with position specificity, in good yield and at high quality level through new intermediate compounds on a commercial scale.

REFERENCE EXAMPLE 1

To a mixture of 2-amino-3',4,4',5-tetramethoxybenzophenone (6.6 g), ethyl 4-chloroacetoacetate (3.7 g) and acetic acid (60 ml) was added concentrated sulfuric acid (0.3 ml) and the mixture was stirred at 100° C. for 3 hours. The reaction mixture was then concentrated under reduced pressure and the residue was poured in water, made basic with 2N—NaOH, and extracted with chloroform. The chloroform layer was washed with water and dried ($MgSO_4$) and the solvent was distilled off under reduced pressure. The residue was subjected to silica gel column chromatography and eluted with chloroform-ethyl acetate (7:3, v/v) to give ethyl 2-chloromethyl-4-(3,4-dimethoxyphenyl)-6,7-dimethoxyquinoline-3-carboxylate (53%). Recrystallization from acetone-ether provided colorless prisms, m.p. 147°–148° C.

REFERENCE EXAMPLE 2

2-Amino-3',4,4',5-tetramethoxybenzophenone hydrochloride (36.0 g) and ethyl 4-chloroacetoacetate (21.4 g) were stirred in ethanol (350 ml) under reflux for 7 hours. After completion of the reaction, triethylamine (10.6 g) was added dropwise at a temperature not over 20° C. and the mixture was stirred at 5° C. for 1 hour. The crystals were collected by filtration, washed twice with 50 ml each of ethanol and dried under reduced pressure to provide ethyl 2-chloromethyl-4-(3,4-dimethoxyphenyl)-6,7-dimethoxyquinoline-3-carboxylate (41.0 g; yield 92%).

EXAMPLE 1

Production of 4-Amino-1-[4-(3,4-dimethoxyphenyl)-3-ethoxycarbonyl-6,7-dimethoxyquinolin-2-ylmethyl]-4H-1,2,4-triazolium Bromide Ethyl 2-chloromethyl-4'-(3,4-dimethoxyphenyl)-6,7-dimethoxyquinoline-3-carboxylate (22.5 g, content 99.1%, 50.0 mmol), sodium bromide (5.81 g, 56.5 mmol) and 4-amino-1,2,4-triazole (5.47 g, 65.1 mmol) were suspended in DMF (50 ml) and stirred at 65° C. for 3 hours.

To this reaction mixture was added ethyl acetate (100 ml) and the resulting crystals were collected by filtration and dried to provide 4-amino-1-[4-(3,4-dimethoxyphenyl)-3-ethoxycarbonyl-6,7-dimethoxyquinolin-2-ylmethyl]-4H-1,2,4-triazolium bromide as white crystals (31.1 g, content 83.6%, yield 90.6%).

After structural identification, the compound was purified by silica gel column chromatography (mobile phase $CH_2Cl_2$:MeOH=5:1) and recrystallization (4.8% EtOH/$H_2O$).

IR ($cm^{-1}$, KBr): 3196, 1706, 1518, 1472. $^1$H-NMR (DMSO-$d_6$, 90 MHz) δ: 0.92 (3H, t, J=6.9 Hz, $CO_2CH_2\underline{CH_3}$), 3.72 (3H, s, OMe), 3.77 (3H, s, OMe), 3.86 (3H, s, OMe), 3.96 (3H, s, OMe), 3.72–4.09 (2H, m, $CO_2\underline{CH_2}$), 5.94 (2H, s, $\underline{CH_2}$N), 6.93–7.31 (7H, m), 9.28 (1H, s, CH=N), 10.41 (1H, s, CH=N). Analysis. Calcd for $C_{25}H_{28}N_5O_6$ Br (0.73 H₂O): C, 51.10; H, 5.05; N, 11.92; Br, 13.60 Found: C, 51.10; H, 4.91; N, 11.88; Br, 13.55. mp: 183.8°–184.4° C.

EXAMPLES 2–8

The procedure of Example 1 was repeated except that different species of reaction solvent and additive were used. The results are shown in Table 1 (the HPLC area percentages were confirmed using the respective reaction mixtures).

TABLE 1

| Example No. | Reaction solvent [mol concentration (M)] | Additive | Temperature (°C) | Time (h) | HPLC area percentate (%) Objective compound | HPLC area percentate (%) Starting compound | Yield (%) |
|---|---|---|---|---|---|---|---|
| 2 | CH₃CN [0.5] | — | 100 | 15 | 87.5 | 6.6 | 93.7 |
| 3 | CH₃CN [0.6] | NaBr | 70 | 3.0 | 61.2 | 34.8 | 93.9 |
| 4 | EtOH [0.2] | — | 100 | 15 | 48.7 | 46.4 | 90.9 |
| 5 | i-PrOH [0.2] | — | 80–100 | 7–12 | 38.6 | 58.1 | 92.1 |
| 6 | DMF [1.0] | — | 80–100 | 8–12 | 88.6 | 0.2 | 88.8 |
| 7 | DMF [1.0] | NaI | 70 | 1.5 | 88.1 | — | 88.1 |
| 8 | DMF [1.0] | NaBr | 70 | 3.0 | 94.1 | 0.01 | 94.1 |

EXAMPLE 9

Production of Ethyl 4-(3,4-Dimethoxyphenyl)-6,7-dimethoxy-2-(1,2,4-triazol-1-ylmethyl)quinoline-3-carboxylate In H₂O (37.5 ml) was suspended 4-amino-1-[4-(3,4-dimethoxyphenyl)-3-ethoxycarbonyl-6,7-dimethoxyquinolin-2-ylmethyl]-4H-1,2,4-triazolium bromide (10.31 g, content 83.6%, 15.0 mmol), followed by addition of concentrated hydrochloric acid (3.8 ml, 45 mmol) and 5.6M NaNO₂/H₂O (4.00 ml, 22.5 mmol) under ice-cooling, and the mixture was stirred at room temperature for 2 hours.

To this reaction mixture was added a neutralizing amount (8.7 ml) of 5N—NaOH and the resulting crystals were collected by filtration and rinsed with water to provide 6.66 g (yield 92.8%) of ethyl 4-(3,4-dimethoxyphenyl)-6,7-dimethoxy-2-(1,2,4-triazol-1-ylmethyl)quinoline-3-carboxylate as white crystals.

IR (cm⁻¹, KBr): 1720, 1504, 1468, 1430. ¹H-NMR (CDCl₃, 90 MHz) δ: 0.89 (3H, t, J=7.1 Hz, CO₂CH₂CH₃), 3.79 (3H, s, OMe), 3.86 (3H, s, OMe), 3.96 (3H, s, OMe), 4.04 (3H, s, OMe), 3.86–4.13 (2H, q, J=7.1 Hz, CO₂CH₂), 5.72 (2H, s, CH₂N), 6.86–6.95 (4H, m), 7.41 (1H, s), 7.93 (1H, s), 8.23 (1H, s). mp: 175.4°–176.0° C.

EXAMPLE 10

Production of Ethyl 4-(3,4-Dimethoxyphenyl)-6,7-dimethoxy-2-(1,2,4-triazol-1-ylmethyl)quinoline-3-carboxylate In H₂O (5.44 l) was suspended 4-amino-1-[4-(3,4-dimethoxyphenyl)-3-ethoxycarbonyl-6,7-dimethoxyquinolin-2-ylmethyl]-4H-1,2,4-triazolium bromide (503 g, content: 80.9% 0.709 mol), followed by addition of concentrated hydrochloric acid (159 g, 1.56 mol) and 0.63M NaNO₂/H₂O (1.46 l, 0.920 mol) under ice-cooling, and the mixture was stirred at room temperature for 3 hours.

To this reaction mixture was added a neutralizing amount (295 ml) of 5N NaOH and the resulting crystals were collected by filtration and rinsed with water to give 329 g (yield: 97.0%) of ethyl 4-(3,4-dimethoxyphenyl)-6,7-dimethoxy-2-(1,2,4-triazol-1-ylmethyl)quinoline-3-carboxylate as while crystals.

COMPARATIVE EXAMPLE 1

To a solution of 1H-1,2,4-triazole (0.558 g) in N,N-dimethylformamide (30 ml) was added sodium hydride in oil and the mixture was stirred at room temperature for 15 minutes. Then, ethyl 2-chloromethyl-4-(3,4-dimethoxyphenyl)-6,7-dimethoxyquinoline-3-carboxylate (3.0 g) was added. The mixture was stirred at 80° C. for 1 hour, after which it was poured in water and extracted with ethyl acetate. The ethyl acetate layer was washed with water and dried (MgSO₄) and the solvent was distilled off under reduced pressure. The residue was subjected to silica gel column chromatography. Form the first eluate with chloroform-methanol (40:1, v/v), ethyl 4-(3,4-dimethoxyphenyl)-6,7-dimethoxy-2-(1,2,4-triazol-1-ylmethyl)quinoline-3-carboxylate (1.7 g, 53%) was obtained. Recrystallization from ethyl acetate-hexane provided colorless prisms, m.p. 176°–177° C.

What is claimed is:

1. A process for producing a compound of general formula (2)

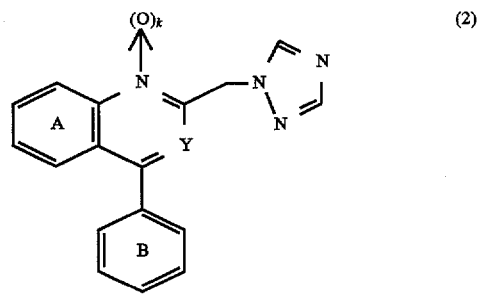

wherein Y represents a nitrogen atom or C-G in which G represents a carboxyl group which may optionally be esterified or amidated, an acyl group, a hydroxyalkyl group which may optionally be protected, or a halogen atom; ring A and ring B each may optionally be substituted; k represents 0 or 1; or a salt thereof, which comprises subjecting a compound of general formula (1)

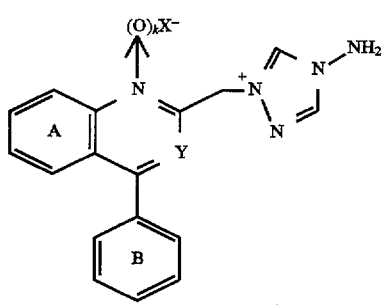 (1)

wherein Y, ring A, ring B, and k are respectively as defined above; X represents a leaving group; or a salt thereof to deamination reaction.

2. A process for producing a compound of general formula (1)

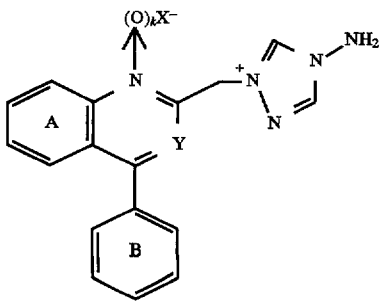 (1)

wherein X represents a leaving group; Y represents a nitrogen atom or C-G in which G represents a carboxyl group which may optionally be esterified or amidated, an acyl group, a hydroxyalkyl group which may optionally be protected, or a halogen atom; ring A and ring B each may optionally be substituted; and k represents 0 or 1; or a salt thereof, which comprises reacting a compound of general formula (3)

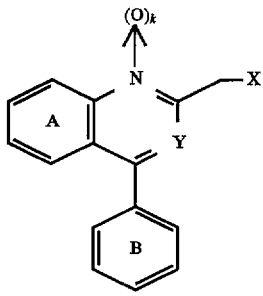 (3)

wherein X, Y, ring A, ring B and k are respectively as defined above; or a salt thereof with 4-amino-1,2,4-triazole.

3. A process for producing a compound of general formula (2)

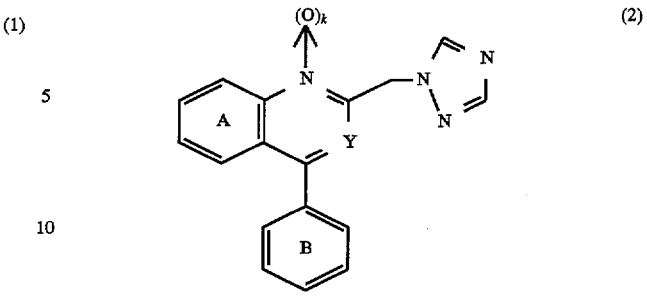 (2)

wherein Y represents a nitrogen atom or C-G in which G represents a carboxyl group which may optionally be esterified or amidated, an acyl group, a hydroxyalkyl group which may optionally be protected, or a halogen atom; ring A and ring B each may optionally be substituted; and k represents 0 or 1; or a salt thereof, which comprises reacting a compound of general formula (3)

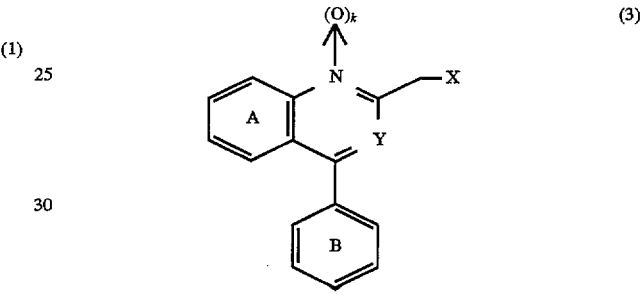 (3)

wherein X, Y, ring A, ring B and k are respectively as defined above; or a salt thereof with 4-amino-1,2,4-triazole to give a compound of general formula (1)

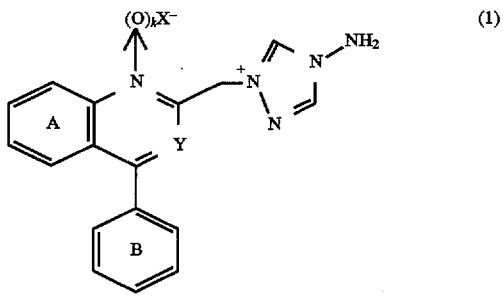 (1)

wherein X, Y, ring A, ring B, and k are respectively as defined above; or a salt thereof and subjecting the last-mentioned compound or salt thus obtained to deamination reaction.

4. The process according to claim 1, wherein said deamination reaction is conducted using nitrous acid.

5. The process claimed in claim 2, wherein X is a halogen atom.

6. The process claimed in claim 1, wherein the compound of general formula (2) is ethyl 4-(3,4-dimethoxyphenyl)-6,7-dimethoxy-2-(1,2,4-triazol-1-yl methyl)quinoline-3-carboxylate.

7. A compound of general formula (1)

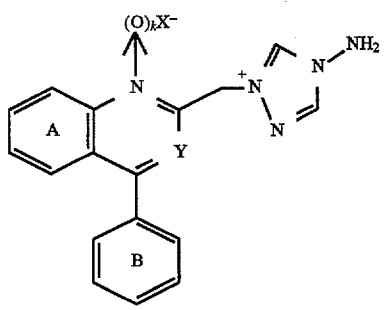

wherein Y represents a nitrogen atom or C-G in which G represents a carboxyl group which may optionally be esterified or amidated, an acyl group, a hydroxyalkyl group which may optionally be protected, or a halogen atom; ring A and ring B each may optionally be substituted; k represents 0 or 1; X represents a leaving group; or a salt thereof.

8. The compound or salt claimed in claim 7, wherein Y represents C-G, where G represents alkyloxycarbonyl.

9. The compound or salt claimed in claim 8, wherein G represents ethoxycarbonyl.

10. The compound or salt claimed in claim 7, wherein ring A is substituted by two alkoxy groups which may be the same or different.

11. The compound or salt claimed in claim 7, wherein ring A is substituted by two methoxy groups.

12. The compound or salt claimed in claim 7, wherein ring B is substituted by two alkoxy groups which may be the same or different.

13. The compound or salt claimed in claim 7, wherein ring B is substituted by two methoxy groups.

14. The compound or a salt thereof of general formula (1) claimed in claim 7, which is 4-amino-1-[4-(3,4-dimethoxyphenyl)-3-ethoxycarbonyl-6,7-dimethoxyquinolin-2-ylmethyl]-4H-1,2,4-triazolium bromide.

* * * * *